Figure 1A:
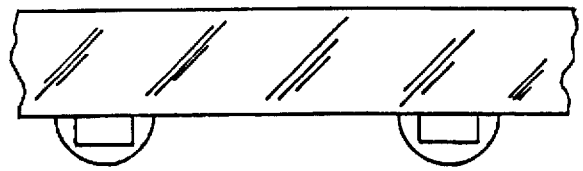

United States Patent

Ershov et al.

[11] Patent Number: 5,741,700
[45] Date of Patent: Apr. 21, 1998

[54] METHOD OF IMMOBILIZING WATER-SOLUBLE BIOORGANIC COMPOUNDS ON A CAPILLARY-POROUS CARRIER

[75] Inventors: Gennady Moiseevich Ershov; Eduard Nikolaevich Timofeev; Igor Borisovich Ivanov; Vladimir Leonidovich Florentiev; Andrei Darievich Mirzabekov, all of Moscow, Russian Federation

[73] Assignee: University of Chicago, Chicago, Ill.

[21] Appl. No.: 411,711

[22] PCT Filed: Aug. 5, 1994

[86] PCT No.: PCT/RU94/00178

§ 371 Date: Jun. 2, 1995

§ 102(e) Date: Jun. 2, 1995

[87] PCT Pub. No.: WO95/04833

PCT Pub. Date: Feb. 16, 1995

[30] Foreign Application Priority Data

Aug. 11, 1993 [RU] Russian Federation ............ 93040901

[51] Int. Cl.⁶ .................. C12M 1/00; C12Q 1/68; A61K 38/00; C07H 19/00
[52] U.S. Cl. .................. 435/287.1; 435/6; 435/287.2; 435/287.9; 530/300; 536/22.1; 536/23.1; 536/25.3; 536/25.4
[58] Field of Search .......... 435/6, 287.1, 287.2, 435/287.9; 536/23.1, 22.1, 25.3, 25.4; 530/300

[56] References Cited

U.S. PATENT DOCUMENTS 5,216,126  6/1993  Cox et al. ............................ 530/350
5,279,821  1/1994  Hirayama et al. ................... 424/78.17

FOREIGN PATENT DOCUMENTS

WO A1 90/10716  9/1990  WIPO.
WO A1 92/10587  6/1992  WIPO.
WO A2 93/04199  4/1993  WIPO.

OTHER PUBLICATIONS

Matthews et al. "Review Analytical strategies for the use of DNA probes" Analytical biochemistry, vol. 169, pp. 1–25, Feb. 1988.

Primary Examiner—Ardin H. Marschel
Assistant Examiner—Jezia Riley
Attorney, Agent, or Firm—Reinhart, Boerner, Van Deuren, Norris & Rieselbach, s.c.

[57] ABSTRACT

The method for immobilizing water-soluble bioorganic compounds to capillary-porous carrier comprises application of solutions of water-soluble bioorganic compounds onto a capillary-porous carrier, setting the carrier temperature equal to or below the dew point of the ambient air, keeping the carrier till appearance of water condensate and complete swelling of the carrier, whereupon the carrier surface is coated with a layer of water-immiscible nonluminescent inert oil and is allowed to stand till completion of the chemical reaction of bonding the bioorganic compounds with the carrier.

4 Claims, 2 Drawing Sheets

METHOD OF IMMOBILIZING WATER-SOLUBLE BIOORGANIC COMPOUNDS ON A CAPILLARY-POROUS CARRIER

FIELD OF THE INVENTION

The present invention relates in general to molecular biology and more specifically to a method for immobilizing water-soluble bioorganic compounds onto a capillary-porous carrier.

BACKGROUND OF THE INVENTION

Known in the present state of the art are quite a number of chemical methods for immobilizing water-soluble bioorganic compounds, e.g., proteins, peptides, and DNA fragments (oligonucleotides and polynucleotides) on capillary-porous carriers. The methods are based on establishing covalent bonds between the bioorganic compound and the carrier. Used as the carrier are: cellulose, carboxymethylcellulose, agarose, dextran, polyaminopolystyrene, polyacrylamides and their derivatives, and others.

One state-of-the-art method for immobilizing oligonucleotides on a capillary porous carrier, namely on a gel matrix (SU, A No. 1,794,088), consists in that the drops of a solution of oligonucleotides are applied to an air-dried gel matrix with the aid of a micromanipulator provided with a dispenser, whereupon the matrix with the solution of oligonucleotides applied thereto is placed in a wet chamber for 4 hours till completion of the reaction of bonding oligonucleotides to gel. Then the matrix is dried for 0.5 hour in the open air, washed with a hybridization buffer (1M NaCl, 10 mM $Na_3 PO_4.7H_2O$, pH 7.0, 1 mM ethylenediaminetetraacetic acid), rinsed with water, and stored dry at minus 20° C. Oligonucleotides are immobilized on a gel matrix, said gel being applied to the substrate, as areas (square cells) spaced from one another.

The chemical reaction of oligonucleotide-to-gel bonding is conducted as follows. Used as a linking agent is 3-methyluridine bound by a 5'–3' internucleotide phosphodiester bond to the oligonucleotide to be immobilized. 3-methyluridine is given preference due to its inability of forming strong hydrogen bonds with any naturally occurring bases.

Prior to applying the gel to the matrix, oligonucleotides containing 3-methyluridine at their 3'-end are oxidized with 1 mM sodium periodate for one hour at room temperature, precipitated with 10 volumes of 2% $LiClO_4$ (lithium perchlorate) in acetone, and dissolved in water.

Oxidation of oligodeoxynucleotide results in formation of a derivative carrying a dialdehyde group at the 3'-end. Before use, the gel matrix is treated with 50% hydrazine whereby a part of the amide groups are substituted by the hydrazide ones which readily react with 3'-dialdehyde to yield a stable morpholine derivative.

The course of immobilization is monitored against the marker ($5'-^{32}P$) introduced with the aid of kinase, into the oligonucleotides being immobilized. The immobilization yield (i.e., the percentage of the oligonucleotide irreversibly bonded with the gel) is close to 80%.

The aforediscussed method, however, has a restriction on its application whenever it is necessary to immobilize a great number (above 10) of various nucleotides, contained in microvolumes (up to tens of nanoliters) of solutions located in the cells (measuring up to 100 μm) of a dense polyacrylamide gel micromatrix, with the cell spacing up to 200 μm when strictly single-type nucleotides are to be placed in each cell. In this case standard conditions for the reaction of covalent bonding of oligonucleotides with the carrier are difficult to attain in all the cells of the matrix, due to inescapable partial evaporation of solutions in some of the cells long before the reaction is completed and often already in the process of applying the solutions and during transfer of the micromatrix to a wet chamber. Thus, the quality of immobilization and, accordingly, that of the micromatrix are affected, the consumption of expensive reagents is increased and the process becomes more costly.

Furthermore, the moisture-exchange process on the matrix surface becomes difficult to control after the matrix has been placed in the wet chamber where water condensate may fall abundantly from the vapor-gaseous phase upon the micromatrix surface and connect the adjoining matrix cells, or the solution may vaporize to such an extent that the reaction would stop. Both such cases will result in a complete loss of the micromatrix. All discussed above shows that practical realization of the aforesaid method is rather complicated.

DISCLOSURE OF THE INVENTION

The present invention has for its principal object to modify the procedures of the method for immobilizing water-soluble bioorganic compounds on a capillary-porous carrier in such a way as to rule out a possibility of liquid evaporation during immobilization and to ensure that covalent bonding between oligonucleotides and the gel matrix proceeds to completion, thereby rendering the process less labor-consuming and the technology suitable for automation and mass production.

The foregoing object is accomplished due to the fact that in a method proposed herein and aimed at mobilization of water-soluble bioorganic compounds to a capillary-porous carrier, comprising application of water-soluble bioorganic compounds to a capillary-porous carrier, for a time necessary to complete the chemical bonding of said bioorganic compounds with the carrier, the carrier temperature is set to be equal to or below the dew point of the ambient air, and the carrier is allowed to stand until water condensate appears and the carrier gets swollen completely, whereupon the carrier surface is coated with a layer of water-immiscible nonluminescent inert oil and is let to stand until the reaction of bonding the bioorganic compounds with the carrier is completed.

It is preferable to use oligonucleotides or polynucleotides as the water-soluble bioorganic compounds and make use of polyacrylamide gel as the capillary-porous carrier.

It is also practical to keep the carrier under an oil layer for at least 48 hours.

All described above makes it possible to rule out a possibility of liquid evaporation during immobilization and to carry out the chemical binding of bioorganic compounds to the carrier till completion.

The method proposed herein is characterized by simplified techniques compared with the known method, it also gives a better quality of immobilization and improved reproducibility.

The method proposed herein is less labor-consuming, it can be readily automated and may be used for mass production.

A BRIEF DESCRIPTION OF THE DRAWINGS

Figure 1B:
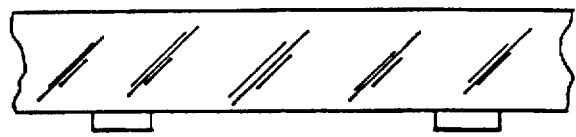
Figure 1C:
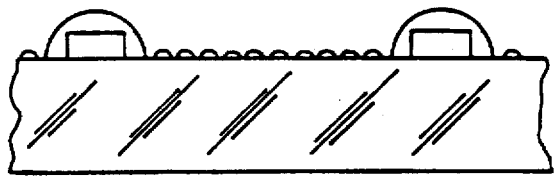
Figure 1D:
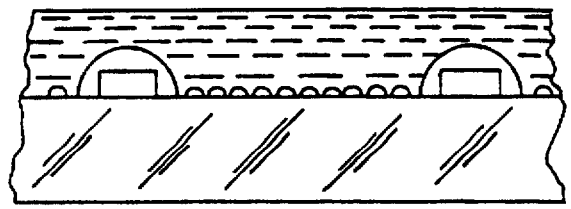
Figure 2:
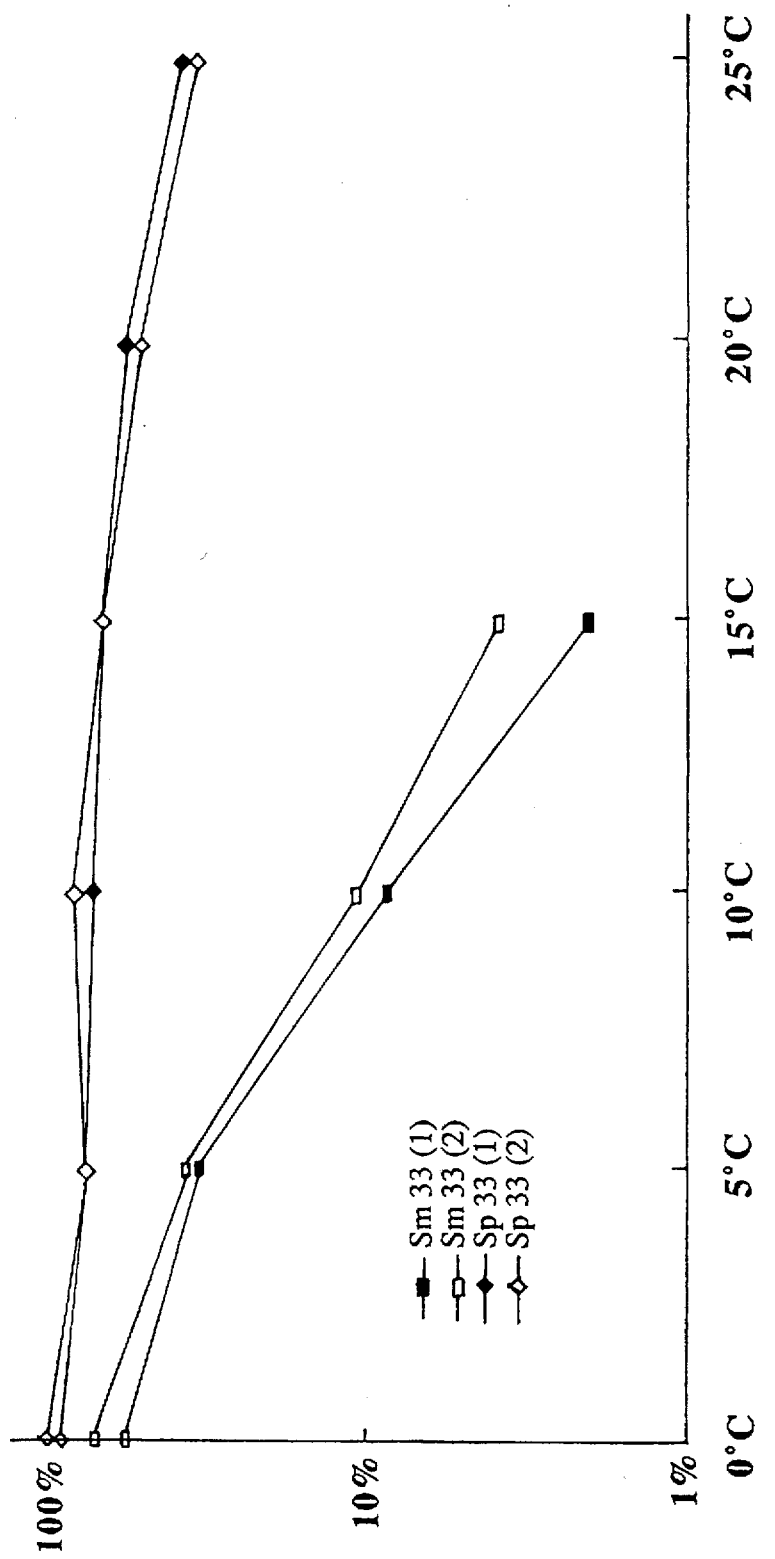

In the following, the invention is illustrated by a detailed description of some specific embodiments thereof with reference to the accompanying drawings, wherein:

FIG. 1A, B, C, D is a sectional side view of a fragment of the carrier (i.e., micromatrix) shown during the process of immobilization, where:

FIG. 1A. a fragment of the micromatrix at the instant when microvolumes of the solutions of bioorganic compounds are loaded thereto;

FIG. 1B. a fragment of the micromatrix at the instant of completion of loading;

FIG. 1C. a fragment of the micromatrix at the instant of setting its temperature equal to or below the dew point of the ambient air;

FIG. 1D. a fragment of the micromatrix after its having been coated with the film of an inert nonluminescent oil;

FIG. 2 presents washing curves of perfect and imperfect duplexes obtained on the micromatrix after hybridization with immobilized nucleotides.

BEST MODE OF CARRYING OUT THE INVENTION

The method proposed herein can be implemented as follows.

The microvolumes of bioorganic solutions, such as oligonucleotides, polynucleotides, water-soluble proteins, peptides, etc. are applied to the surface of a capillary-porous carrier, that is micromatrix. Used as the carrier can be cellulose, carboxymethylcellulose, agarose, dextran, polyaminopolystyrene, and others, though used preferably is polyacrylamide gel.

Once the microvolumes of the solutions of bioorganic compounds have been applied to all cells of the matrix, the micromatrix temperature is set equal to or below the dew point of the ambient air, and is maintained so till swelling of the gel is complete, and noncoalescent droplets of water condensate appear in the spacings between the cells, whereupon a thin layer of an inert nonluminescent oil is cautiously applied to the micromatrix surface, the thickness of the latter layer being over 100 μm. As an oil can be used purified Vaseline; phenyl (10%) methylsilicone oil; phenyl (20%) methylsilicone oil, and others. Thereupon the micromatrix is kept under the oil layer till total completion of the immobilization process, preferably at least for 48 hours. Then the oil is removed with a solvent, e.g. chloroform, and the matrix is dried and stored ready-for-use.

For the sake of better clarity, the process is illustrated in FIG. 1A, B, C, D, wherein a fragment of the micromatrix is shown in a sectional side-elevation view:

FIG. 1A. At the instant when microvolumes of bioorganic solutions are being loaded to the micromatrix cells, the temperature of the micromatrix is maintained equal to that of the ambient air.

FIG. 1B. At the instant of completion of the loading, all droplets have evaporated, the condition of the gel is the same in all cells.

FIG. 1C. At the instant when the water condensation from the ambient air has been completed, the temperature of the micromatrix is below or equal to the dew point of the ambient air. The gel cells have swollen and are coated with water condensate. Minute droplets of condensate have appeared in the intercell spacings, said droplets not coalescing with one another.

FIG. 1D. The micromatrix is coated with the film of a nonluminescent oil, over 100 μm-thick. The temperature of the micromatrix is equal to that of the ambient air.

The herein-proposed method is applicable for immobilizing any water-soluble bioorganic substances to the carrier, especially in cases which require the presence and retention of the liquid (aqueous) phase for a complete progress of chemical reaction of covalent bonding in the system 'substance-carrier'.

For better understanding of the present invention a specific exemplary embodiment thereof is given below.

EXAMPLE 1

Prepare solutions of oligonucleotides Sp-33 (3'CCGTCCAA5'), Sm–33 (3'CCGTCTAA5') having a concentration of 60 pmole per μl, and containing 3-methyluridine at the 3'-end, oxidate them with 1 mM sodium periodate for one hour at room temperature and precipitate with 10 volumes of 2% $LiClO_4$ in acetone, and a solution of a succinimide derivative of tetramethylrhodamine in dimethylsulfoxide with a concentration of 0.5 to 1 μg per 100 μl, which serves for quality control of microdose application. Using a 8% polyacrylamide gel, 30 μm-thick, a micromatrix is formed from the gel, consisting of 100×100-μm cells spaced by 200×200 μm void areas, and is treated with 50% hydrazine for an hour at room temperature, after which microvolumes of the prepared solutions are applied to the surface of the gel cells, namely 1.4±0.29 nl per cell (FIG. 1A). The temperature of the micromatrix is not controlled and equals the temperature of the ambient air (room temperature, FIG. 1B). After applying the microvolumes of the solutions of oligonucleotides to all cells, the temperature of the micromatrix is set to be equal to or below the dew point of the ambient air during the process, and is maintained so until the gel swells completely and noncoalescent water condensate appears in the intervals between the cells (FIG. 1C). Then the surface of the micromatrix is carefully coated with a thin (over 100 μm) layer of nonluminescent phenyl (10%) methylsilicone oil saturated with distilled water, after which the micromatrix is kept under a layer of oil at room temperature until a total completion of the immobilization process, that is, for 48 hours (FIG. 1D). Then the oil is removed with a solvent (chloroform), and the matrix is dried and put into storage.

Since immobilization of bioorganic compounds on carriers is carried out with a principal purpose of further use of thus-obtained system for specific chemical bonding of other bioorganic compounds for their accretion or identification, the quality of immobilization can be assessed by an indirect method. In this particular case, such an assessment is carried out against hybridization of the prepared oligonucleotide micromatrix with a fragment of DNA fluorescent-labeled at the 5'-end and consisting of 19 bases (5'-CCTGGGCAGGTTGGTATCA-3'), which is contained in a buffer solution (1 M NaCl; 10 mM sodium phosphate; 1 mM EDTA; pH=6.8). Then the solution (1 μl per four cells) is applied to the surface of the oligonucleotide micromatrix cooled down to 0° C. To provide a complete hybridization, the matrix is allowed to stand under these conditions for two hours, whereupon the hybridization solution containing DNA fragments is washed out with a cooled 1 M NaCl solution. The surface of the matrix is coated with a thin layer of cooled 1 M NaCl solution; a cover slide is placed on the matrix and the latter is put on a thermostated table of a fluorescence microscope provided with a CCD camera, and a computer-aided image processing system. Then a measurement cycle is conducted, the image of the micromatrix is recorded in the temperature range from 0° to 25° C. by 5° C. steps (including the margins of the range) and with a four minute exposure at each step. Then the image is analyzed, and the signal measured by the CCD camera is averaged in the region corresponding to each cell of the micromatrix, a maximum error being within 5%. The background is assessed by the signals from the points situated in the immediate vicinity of the analyzed cell, the error being within 15%. The background value is subtracted from the thus-obtained signal values, and the result is divided by the frame accumulation time (preset during the measuring cycle). All results are expressed in percent against the brightest cell and are graphically represented in FIG. 2B as washout curves of perfect (Sp-33 3'CCGTCCAA5') and imperfect (Sm-33 3'CCGTCTAA5') duplexes obtained on the micromatrix (four cells) after hybridization with immobilized oligonucleotides. FIG. 2 presents the remaining duplexes as ordinate (%), and the washout temperature as abscissa (°C.).

It is known that the amount of hybridized oligonucleotide is variable and will depend (all other factors being equal) on the oligonucleotide composition and, when the amount of the immobilized oligonucleotide and the composition thereof are equal, on the local conditions in a specific cell (i.e., the state of the carrier structure, accuracy of geometric size, presence of admixtures, etc.). That is why some difference is observed in the level of signals at the initial point (0° C.) in FIG. 2 even for oligonucleotides of the same composition. Thus, the indirect method for assessing the immobilization quality (from hybridization) results in a slight under estimation.

It is evident from the resultant curves of Sp-33 (1, 2) and Sm-33 (1, 2) in the chart of FIG. 2 that the obtained data on hybridization and hence immobilization are sufficient, both quantitatively and qualitatively, for unambiguously identifying the DNA fragment under test (high level of the initial hybridization signal at 0° C. and disappearance of the signal for Sm-33 (1, 2) at 15° C. with a high signal level retained for Sp-33 (1, 2).

Similar curves have been obtained for a great number of various duplexes (not shown), while the immobilization quality in all cases was no worse than in the Example cited before, and the reproducibility was 100% in all experiments. This demonstrates high reproducibility and quality of the immobilization method being proposed herein.

Industrial Applicability

The present invention finds application in medicine, molecular biology, agriculture for genetic diagnosis, sequencing and mapping of DNA, detecting of mutations, and so on.

We claim:

1. A method for immobilizing water-soluble bioorganic compounds on to a carrier bondable with the compounds, comprising applying water-soluble bioorganic compounds onto a bondable carrier having a matrix of cells and kept thereon until completion of the chemical bonding between said bioorganic compounds and said carrier matrix, application of water-soluble bioorganic solutions being followed by setting the temperature of the carrier equal to or below the dew point of the ambient air and the carrier is allowed to stand until water condensate swells said matrix cells, whereupon the carrier surface is coated with a layer of water-immiscible nonluminescent inert oil and allowed to stand until the reaction of bonding the bioorganic compounds with the carrier is completed.

2. A method according to claim 1 wherein the bioorganic compounds are selected from the group consisting of oligonucleotides and polynucleotides.

3. A method according to claim 1 wherein said carrier comprises polyacrylamide gel.

4. A method according to claim 1 wherein said carrier is kept under said oil layer for about 48 hours.

* * * * *

UNITED STATES PATENT AND TRADEMARK OFFICE
CERTIFICATE OF CORRECTION

PATENT NO.    : 5,741,700

DATED         : April 21, 1998

INVENTOR(S)   : Ershov et al.

It is certified that error appears in the above-identified patent and that said Letters Patent is hereby corrected as shown below:

Title page, after "Attorney, Agent, or Firm–" delete "Reinhart, Boerner, Van Deuren, Norris & Rieselbach, s.c." and insert --Michael D. Rechtin, Foley & Lardner--.

Title page, line 2 of the ABSTRACT, after "to" insert --a--.

In Column 1, line 4, insert --The United States Government has rights in this invention pursuant to funding from the U.S. Department of Energy and The University of Chicago.--.

In Column 2, line 34, delete "mobilization" and insert --immobilization--.

In Column 3, line 1, delete "FIG." and insert --FIGS.--.

In Column 3, line 1, delete "is a" and insert --are--.

In Column 3, line 1, delete "view" and insert --views--.

In Column 3, line 4, after "1A" insert --is--.

In Column 3, line 7, after "1B" insert --is--.

In Column 3, line 9, after "1C" insert --is--.

In Column 3, line 12, after "1D" insert --is--.

In Column 3, line 12, delete "its" after "after".

In Column 3, lines 18-19, delete "BEST MODE OF CARRYING OUT THE INVENTION" and insert --DETAILED DESCRIPTION OF PREFERRED EMBODIMENTS--.

In Column 3, line 33, delete "so till" and insert --until--.

In Column 3, line 38, delete "As an oil" and insert --The following oils--.

In Column 3, line 38, insert a colon --:-- after "used".

UNITED STATES PATENT AND TRADEMARK OFFICE
CERTIFICATE OF CORRECTION

PATENT NO. : 5,741,700

DATED : April 21, 1998

INVENTOR(S) : Ershov et al.

It is certified that error appears in the above-identified patent and that said Letters Patent is hereby corrected as shown below:

In Column 3, line 44, delete "ready-for-use" and insert --ready for use--.
In Column 3, line 46, delete "FIG." And insert --FIGS.--.
In Column 4, line 18, delete "a" and insert --an--.
In Column 4, line 32, delete "the-cells" and insert --the cells--.
In Column 5, line 26, delete "under estimation" and insert --underestimation--.
In Column 6, line 15, delete "on to" and insert --onto--.

Signed and Sealed this

Thirteenth Day of October 1998

Attest:

BRUCE LEHMAN

Attesting Officer

Commissioner of Patents and Trademarks